United States Patent
Ponce et al.

(10) Patent No.: US 7,306,930 B2
(45) Date of Patent: Dec. 11, 2007

(54) METHOD BACTERIAL ENDOSPORE QUANTIFICATION USING LANTHANIDE DIPICOLINATE LUMINESCENCE

(75) Inventors: Adrian Ponce, Altadena, CA (US); Kasthuri J. Venkateswaran, Arcadia, CA (US); James Patrick Kirby, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 515 days.

(21) Appl. No.: 10/306,331

(22) Filed: Nov. 27, 2002

(65) Prior Publication Data

US 2003/0138876 A1   Jul. 24, 2003

Related U.S. Application Data

(60) Provisional application No. 60/334,463, filed on Nov. 30, 2001.

(51) Int. Cl.
 *C12Q 1/04* (2006.01)
(52) U.S. Cl. ........................................ 435/34
(58) Field of Classification Search ................ 435/7.1, 435/7.32, 34, 39, 40.5, 832, 968
 See application file for complete search history.

(56) References Cited

U.S. PATENT DOCUMENTS

| | | | |
|---|---|---|---|
| 4,560,665 A | 12/1985 | Nakae et al. | 436/172 |
| 4,943,522 A | 7/1990 | Eisinger et al. | 435/7.25 |
| 4,965,211 A | 10/1990 | Wieder et al. | 436/543 |
| 5,124,268 A | 6/1992 | Dakubu | 436/537 |
| 5,792,330 A | 8/1998 | Petersen et al. | |
| 5,830,769 A | 11/1998 | Wieder et al. | 436/536 |
| 5,876,960 A | 3/1999 | Rosen | |
| 6,136,549 A | 10/2000 | Feistel | 435/7.1 |
| 6,242,268 B1 | 6/2001 | Wieder et al. | 436/538 |
| 6,569,630 B1 | 5/2003 | Vivekananda et al. | 435/6 |
| 6,599,715 B1 | 7/2003 | Vanderberg et al. | 435/34 |
| 2002/0135772 A1 | 9/2002 | Bornhop et al. | |
| 2003/0064427 A1 | 4/2003 | Felkner et al. | 435/31 |
| 2003/0138876 A1 | 7/2003 | Ponce et al. | 435/34 |
| 2004/0014154 A1 | 1/2004 | Ponce et al. | 435/7.32 |

FOREIGN PATENT DOCUMENTS

| | | |
|---|---|---|
| WO | WO 00/63422 | 10/2000 |
| WO | 01/83561 A2 | 11/2001 |
| WO | 03/024491 A2 | 3/2003 |
| WO | 03/065009 A2 | 8/2003 |
| WO | 03/067211 | 8/2003 |

OTHER PUBLICATIONS

Elbanowski et al. 1996.The Lanthanides As Luminescent Probes In Investigation Of Biochemical Systems, Journal of Photochemistry and Photobiology A: Chemistry, vol. 99, pp. 85-92.*
Lamture et al. 1995. Intensely Luminescent Immunoreactive Conjugates of Proteins and Dipicolinate—Based Polymeric Tb (III) Chelates. Bioconjugate Chemistry, vol. 6, pp. 88-92.*
Beverly, M.B., et al., "Analysis of Dipicolinic Acid in Bacterial Spores by Electron Monochromator-Mass Spectrometry," *Presented at the 47th ASMS Conference on Mass Spectrometry and Allied Topics*, Dallas, Texas, 2 pages total (Jun. 13-17, 1999).
"Bio-Threat Alert (BTA™) Strips," 1 page total (Spring 2001).
Hindle, A., et al., "Dipicolinic Acid (DPA) Assay Revisited and Appraised for Spore Detection," *Analyst*, vol. 124, pp. 1599-1604 (1999).
Paratamian, S.A., "Anthrax Detection, The Faster, The Better," *Microbiology 12*, INTERNET: <http://www.college.ucla.edu/webproject/micro12/honorprojects/Partamianp01/MicroHonorsWebPage.html> pp. 1-8 (Spring 2001).
Abstract of Scholl, P., et al., "Immunoaffinity Based Phosphorescent Sensor Platform for the Detection of Bacterial Spores," *Proceedings of the SPIE*, vol. 3913, 1 page total (2002).
Sorasaenee, K., et al., "Cooperative Binding of Tb(III) Supramolecular Complexes with Dipicolinic Acid: Improved Sensitivity of Metal-Contaning Lumophores in Biomedical Applications," *Division of Chemistry and Chemical Engineering, California Institute of Technology*, Pasadena, California, 1 page total (2003).

(Continued)

*Primary Examiner*—Jon Weber
*Assistant Examiner*—Kailash Srivastava
(74) *Attorney, Agent, or Firm*—Ladas & Parry, LLP

(57) ABSTRACT

A lanthanide is combined with a medium to be tested for endospores. The dipicolinic acid released from the endospores binds the lanthanides, which have distinctive emission (i.e., luminescence) spectra, and are detected using photoluminescence. The concentration of spores is determined by preparing a calibration curve generated from photoluminescence spectra of lanthanide complex mixed with spores of a known concentration. A lanthanide complex is used as the analysis reagent, and is comprised of lanthanide ions bound to multidentate ligands that increase the dipicolinic acid binding constant through a cooperative binding effect with respect to lanthanide chloride. The resulting combined effect of increasing the binding constant and eliminating coordinated water and multiple equilibria increase the sensitivity of the endospore assay by an estimated three to four orders of magnitude over prior art of endospore detection based on lanthanide luminescence.

8 Claims, 4 Drawing Sheets

OTHER PUBLICATIONS

Warth, A.D., "Liquid Chromatographic Determination of Dipicolinic Acid from Bacterial Spores," *Applied and Environmental Microbiology*, vol. 38, No. 6, pp. 1029-1033 (Dec. 1979).

Gómez-Hens, A., et al., "Terbium-Sensitized Luminescence: A Selective and Versatile Analytical Approach," *Trends in Analytical Chemistry*, vol. 21, No. 2, pp. 131-141 (2002).

Rosen, D.L., "Bacterial Endospore Detection Using Photoluminescence From Terbium Dipicolinate," *Reviews Analytical Chemistry*, vol. 18, No. 1-2 (1999).

Pierson, D., et al., "Microbial Contamination of Spacecraft", *Gravitational and Space Biology Bulletin* 14 (2) (Jun. 2001).

Rode, et al., "Induced Release of Dipicolinic Acid From Spores of *Bacillus megaterium*", *Journal of Bacteriology*, vol. 79, pp. 650-656 (1960).

Rose, L., et al., "Swab Materials and Bacillus Anthracis Spore Recovery from Nonporous Surfaces", *Emerging Infectious Diseases*, vol. 10, No. 6, www.cdc.gov/eid (Jun. 2004).

Sacks, L.E., "Chemical Germination of Native and Cation-Exchanged Bacterial Spores with Trifluoperazine," *Applied and Environmental Biology*, vol. 56, No. 4, pp. 1185-1187 (1990).

Xiao, M., et al., "An improved instrument for measuring time-resolved lanthanide emission and resonance energy transfer", *Review of Scientific Instruments*, vol. 70, No. 10 (Oct. 1999).

Selvin, P.R., "The Renaissance of Flourescense Resonance Energy Transfer", *Natural Structural Biology*, vol. 7, No. 9, pp. 730-734 (2000).

Singh, R., "Microbial Diversity of Biofilms in Dental Unit Water System", *Applied and Environmental Microbiology*, pp. 3412-3420 (Jun. 2003).

Uchida, I., et al., "Cloning and Characterization of a Gene Whose Product Is a trans-Activator of Anthrax Toxin Synthesis", *Journal of Bacteriology*, vol. 175, No. 17 (Sep. 1993).

Vaid, A., et al., "The destruction by microwave radiation of bacterial endospores and amplification of the released DNA", *Journal of Applied Microbiology*, vol. 85, pp. 115-122 (1998).

Vereb, G., et al., "Temporarily and Spectrally Resolved Imaging Microscopy of Lanthanide Chelates", *Biophysical Journal*, vol. 74, pp. 2210-2222 (May 1998).

Xiao, M., et al., "An improved instrument for measuring time-resolved lanthanide emission and resonance energy transfer", *Review of Scientific Instruments*, vol. 70, No. 10 (Oct. 1999).

Beeby, A., et al., "Luminescence imaging microscopy and lifetime mapping using kinetically stable lanthanide (III) complexes", *Journal of Photochemistry and Photobiology*, B: Biology 57, pp. 83-89 (2000).

Branda, S., et al., "Fruiting body formation by *Bacillus subtilis*," *PNAS*, vol. 98, No. 20, 11621-11626 (Sep. 25, 2001).

Horrocks Jr., W., et al., "Lanthanide Ion Luminescense Probes of the Structure of Biological Macromolecules", *American Chemical Society*, No. 14, pp. 384-392 (1981).

Koehler, T.M., "*Bacillus anthracis* Genetics and Virulence Gene Regulation," *Current Topics in Microbiology & Immunology*, vol. 271, pp. 143-164, publication year not given.

Lester, E., et al., "An Anthrax "Smoke" Detector", *IEEE Engineering in Medicine and Biology*, pp. 38-42 (Sep./Oct. 2002).

Lutterbach, M.T.S., et al., "Biofilm formation on Brass Coupons Exposed to Cooling Water", *Brazilian Journal of Chemical Engineering*, vol. 14, No. 1 (Mar. 1997).

Lutterbach, M.T.S., et al., "Biofilm Formation Monitoring in an Industrial Open Water Cooling System," *Revista de Microbiologia*, 28, pp. 106-109 (1997).

Mitchell, A.C., et al., "Measurement of nanosecond time-resolved fluorescence with a directly gated interline CCD camera",Journal of Microscopy, vol. 206, Pt. 3, pp. 233-238 (Jun. 2002).

Murrell, W. G., *Chemical Composition of Spores and Spore Structures* Chapter 7, pp. 215-243, year not given.

Nicholson, W.L., et al., "Resistance of Bacillus Endospores to Extreme Terrestrial and Extraterrestrial Environments", *Microbiology and Molecular Reviews*, vol. 64, No. 3, pp. 548-572 (Sep. 2000).

Pastuska, J., et al., "Bacterial and fungal aerosol in indoor environment in Upper Silesia, Poland," *Atmospheric Environment*, 34, pp. 3833-3842 (2000).

Branda, S., et al., "Fruiting body formation by *Bacillus subtilis*," *PNAS*, vol. 98, No. 20, 11621-11626 (Sep. 25, 2001).

Lamture, et al., Intensity Luminescent Immunoreactive Conjugates of proteins and Dipicolinate-Based Polumeric Tb (III) Chelates, Biconjugate Chemistry, vol. 6, pp. 88-92 (1995).

Pellegrino, P., et al., "Enhanced spore detection using dipicolinate extaction techniques", Analytica Chimicha Acta, vol. 455, No. 2, pp. 1667-177(Jan. 8, 2002).

Pellegrino, P.M., et al., "Bacterial endospore detection using terbium dipicolinate photoluminescence in the presence of chemical and biological materials", Analytical Chemistry 1998 U.S. Army Res. Lab, vol. 70, No. 9, pp. 1755 (1998).

Pierson, D., et al., "Microbial Contamination of Spacecraft", *Gravitational and Space Biology Bulletin* 14 (2) (Jun. 2001).

Scholl, P., et al., "Immunoaffinity based phosphorescent sensor platform for the detection of bacterial spores", Proc. SPIE Int Soc Opt Eng, Vaol. 3913, pp. 204-214 (2000).

Seveus, et al., "Time-resolved fluorescence imaging of europheu label in immnunohistochemistry and in situ hybridization", Cytometry, 13. pp. 329-338 (1998).

\* cited by examiner

Tb    Tb - DPA

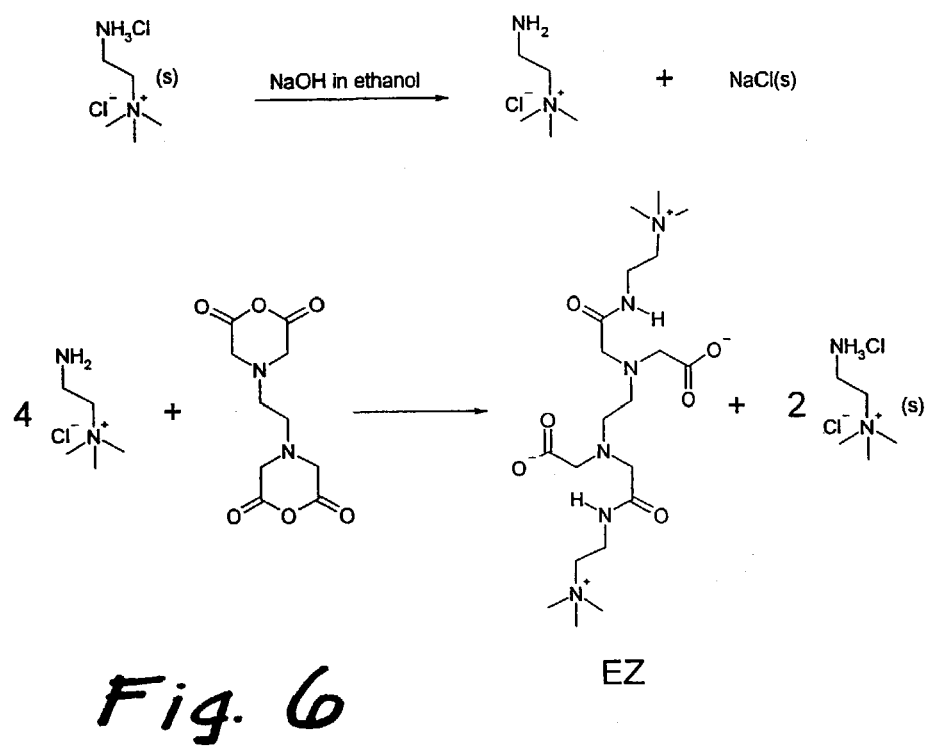
Fig. 6
Fig. 7
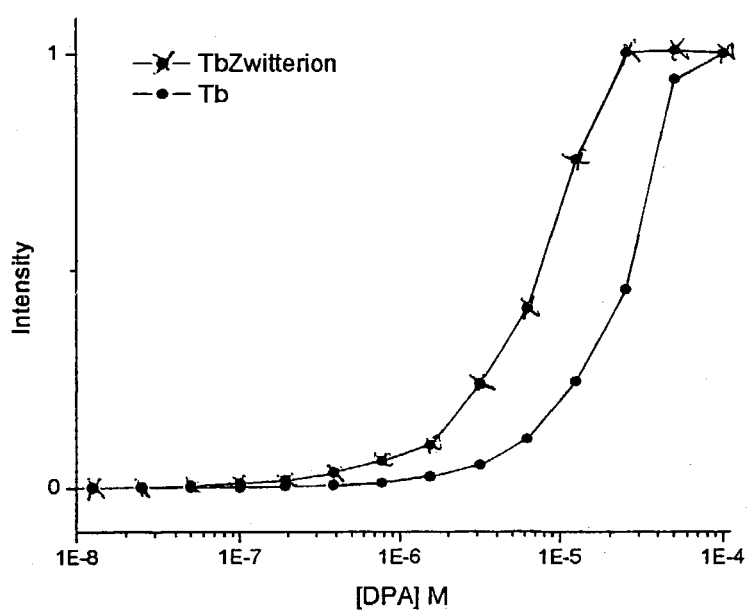

METHOD BACTERIAL ENDOSPORE QUANTIFICATION USING LANTHANIDE DIPICOLINATE LUMINESCENCE

RELATED APPLICATIONS

The present application is related to U.S. Provisional Patent Application, Ser. No. 60/334,463, filed Nov. 30, 2001 which is incorporated herein by reference and to which priority is claimed pursuant to 35 USC 119.

GOVERNMENT RIGHTS

The U.S. Government has certain rights in this invention pursuant to Grant No. NAS7-1407 awarded by NASA.

BACKGROUND OF THE INVENTION

1. Field of the Invention

The invention is directed to improving the sensitivity of technology for the real-time quantification of bacterial endospore levels based on lanthanide dipicolinate luminescence.

2. Description of the Prior Art

An endospore (i.e., bacterial spore or bacterial endospore) is a generalized term for a type of spore that is produced within certain species of bacteria. The primary function of most endospores is to ensure survival through periods of environmental stress. Endospores are drought, heat, and starvation tolerant. They are protected by a hardened shell of protein and carbohydrates and produced by a form of binary fission in bacteria. Hence, endospores are the prime life form for free dispersal of *Bacillus* and *Clostridium* bacterial species in the environment, i.e. dispersal without being hosted by any other life form. The cost and technical difficulty of endospore production has continued to decrease over time, thereby coming with the economic and technological means of a wider segment of the world population, including radical ideological groups incapable of being deterred by possible retaliation and harbored by unofficial transnational political networks unburdened any national identification or responsibility. The need to be able to detect the presence of endospores in the field has become more urgent with this significant proliferation of biotechnologies capable of producing toxic endospores in quantity.

More specifically, certain bacteria can form endospores during times of stress or lack of food. This dormant bacterial form can survive harsh conditions such as boiling, freezing, and desiccation that readily kill vegetative bacteria. Indeed, *Bacillus stearothermophilus* and *Bacillus subtilis* spores are used to check the performance of autoclaves. Two genera of medical importance, *Bacillus* and *Clostridium*, have the ability to develop endospores. They are the causative agents of anthrax, tetanus, botulism, and gas gangrene. Other endospore-producing prokaryotes are found in several genera of soil bacteria such as *Desulfotomaculum*, *Sporolactobacillus*, and *Sporosarcina*. Endospore-forming bacteria are most commonly found in the soil. However, the endospores themselves exist almost everywhere, including the atmosphere, where they may ride on dust particles. The fact that endospores are so hard to destroy is the principal reason for the lengthy and elaborate sterilization procedures that are employed in hospitals, canneries, and other places where sterilization is required.

The current state of the art method requires lengthy and labor intensive methods. Two traditional methods are used to measure the concentration of endospores in a sample—colony counting and direct microscopic counting. The procedure for colony counting to determine endospore concentration consists of heat-shocking the sample to kill vegetative cells while endospores remain viable, plating a known volume of the sample with a known dilution factor onto a growth medium, and incubating the growth plates for 2 days. Finally, the resultant colonies are counted and reported as colony-forming units (CFU's).

The procedure for direct microscopic counting consists of two steps. (1) The sample is placed on a slide with an indentation of a known volume, and the glass surface of the slide is inscribed with squares of known area. (2) The bacteria in each of the several squares are counted and the average count is multiplied by an appropriate factor to yield the number of total cells per milliliter in the original suspension. Bacterial endospores can be specifically identified using microscopic staining methods. However, because the limited field of view of a microscope at high magnifications, searching for stained bacterial cells in low concentrations can take a prohibitive amount of time.

These methods suffer prohibitive difficulties with low-concentration field samples. First, endospores tend to agglomerate on particulates; attached endospores cannot be accurately counted with the traditional methods, even though they could easily represent the bulk of biomass in a field sample. Second, the traditional methods take a long time and are labor-intensive. Finally, colony-counting methods only work for cultivable bacteria, which are in the minority in field samples.

The prior art method of endospore detection was first worked out by L. E. Sacks, "Chemical Germination of Native and Cation-Exchanged Bacterial-Spores with Trifluoperazine," Applied and Environmental Microbiology, vol. 56, pp. 1185-1187, 1990. This was later refined by Rosen, "*Bacterial Spore Detection And Quantification Methods*", U.S. Pat. No. 5,876,960 (1999), which is incorporated herein by reference, has a detection limit of 105 spores/ml, which is too high for many applications to be practical. According to this art, a lanthanide such as europium or terbium is combined with a medium to be tested for endospore content. The lanthanide will react with calcium dipicolinate present in any bacterial spores in the sample medium to produce a lanthanide chelate, specifically, terbium or europium dipicolinate. The lanthanide chelate has distinctive absorbance and emission spectra that can be detected using photoluminescence testing, for example. The occurrence of emission from the sample medium upon excitation at wavelengths distinctive of the lanthanide dipicolinate chelate, thus reveals the presence of spores in the sample medium. The concentration of spores can be determined by preparing a calibration curve that relates absorbance or emission intensities to spore concentrations for test samples with known spore concentrations. The calibration curve can be used to determine the spore concentration of a sample medium using the absorbance or emission intensity for the combined lanthanide-sample medium.

The current state-of-the-art luminescence endospore quantification scheme suffers from low sensitivity, which is limited by the binding constant (i.e., the affinity of dipicolinic acid for binding the lanthanide ion). What is needed is a real-time endospore quantification methodology that is not limited by high detection thresholds. Such an invention has immediate uses in the healthcare field, food preparation/inspection markets and for monitoring biological warfare attacks.

BRIEF SUMMARY OF THE INVENTION

An improved sensitivity for bacterial endospore detection is realized based on dipicolinic acid triggered lanthanide luminescence. A lanthanide is combined with a medium to be tested for endospores. Dipicolinic acid is released from endospores by inducing germination or destructive lysing (e.g., microwaving, autoclaving, chemical oxidation). The released dipicolinic acid binds the lanthanides, which have distinctive emission (i.e., luminescence) spectra, and are detected using photoluminescence measurements. The concentration of spores is determined by preparing a calibration curve that relates emission intensities to spore concentrations for test samples with known spore concentrations. A lanthanide complex is used as the analysis reagent. The lanthanide complex is comprised of the lanthanide ion bound to a multidentate ligand that increase the dipicolinic acid binding constant through a cooperative binding effect with respect to lanthanide chloride (i.e, lanthanide aquo complex in solution). In addition to enhancing dipicolinic acid binding, the deleterious effects of coordinated water and multiple equilibria are also eliminated by encapsulating the lanthanide ions multidentate ligands. The combined effect of increasing the binding constant and eliminating coordinated water and multiple equilibria increase the sensitivity of the endospore assay by an estimated three orders of magnitude over prior art of endospore detection based on lanthanide luminescence.

Dipicolinic acid (DPA, 2,6-pyridinedicarboxylic acid) is present in high concentrations (~1 molar or ~15% of dry weight) in the core of bacterial spores, typically as a 1:1 complex with $Ca^{2+}$ ($K11=10^{4.4}$ $M^{-1}$). DPA is not present in vegetative cells, but is an important constituent of bacterial spores, which extract the $Ca^{2+}$ from the environment. It is released into bulk solution upon germination (the process of spore to vegetative cell transformation). Because DPA is only found in bacterial spores in nature, it serves an indicator molecule for the presence of bacterial spores. Fortuitously, DPA is also a classic inorganic chemistry ligand that binds metal ions with high affinity. DPA binding to terbium ions triggers intense green luminescence under UV excitation. The turn-on of green luminescence signals the presence of bacterial spores, and the intensity of the luminescence can be correlated to the number of endospores per milliliter. Potential interferents such as sugars, nucleic and amino acids are present in much lower concentrations in endospores and vegetative cells and have binding constants for Tb that are many orders of magnitude less than that of DPA ($KA=10^{8.7}$ $M^{-1}$). Thus, this method is relatively immune to these interferents.

The mechanism of this method is based on the unique photophysical properties of lanthanide ions. The luminescence of lanthanide ions is characterized by long lifetimes (0.1 to 1 ms), small extinction coefficients (i.e., absorptivity ~1 $M^{-1}$ $cm^{-1}$) and narrow emission bands. Narrow emission bands arise because the valence f-orbitals are shielded from the environment by the outer s and p electrons, and long lifetimes/small extinction coefficients arise because the transition between the emitting excited state and ground state is highly forbidden. Thus, direct excitation of terbium ions leads to weak luminescence due to the small absorption cross section. However, coordination of organic chromophores, like DPA, triggers intense terbium luminescence. The juxtaposition of DPA, which has an absorptivity of 5000 $M^{-1}$ $cm^{-1}$, serves as a light-harvesting center (i.e., antenna effect). Strong electronic coupling and downhill energetics allow the DPA centered excitation energy to be efficiently transferred to the lanthanide ion, which subsequently luminesces bright green.

The detection limit is improved in the invention by enhancing the binding constant of DPA to Tb. An increased binding constant gives rise to higher fractions of DPA bound to Tb at low DPA concentrations. DPA to Tb binding is required for the green luminescence turn-on, which signals the presence of bacterial spores. The binding constant, K11, is related to the binding strength of the DPA to the Tb complex by the following thermodynamic expression:

$$\Delta G = -RT \ln K11,$$

where $\Delta G$ is the change in Gibbs free energy upon binding, R is the gas constant, T is temperature in Kelvin, and K11 is the binding constant for a 1:1 complex. DPA binding can be enhanced by encapsulating the Tb with a ligand that has recognition sites with attractive binding interactions for the incoming DPA; this is reminiscent of binding pockets in enzymes that exhibit complementary shape and binding interactions for an incoming substrate. We have calculated, based on the above equation, that two average hydrogen bonds will enhance the binding by three orders of magnitude (when water is used as the solvent), which will correspondingly enhance the detection limit. We anticipate that a ligand capable of forming two hydrogen bonds to DPA will lead to detection limits of ~1 spore/ml.

In addition to increasing the DPA to Tb binding constant, these multidentate ligands (i.e., ligands that coordinate with multiple ligating moieties) eliminate the deleterious effects of coordinated water and multiple equilibria. A Tb-ligand complex with a coordination number of 6 (i.e., the ligand coordinates to the lanthanide at six locations) allows only one DPA molecule to bind and the Tb-crown ether DPA complex contains no coordinated water, which increases the quantum yield. The detection limit is increased by approximately an order of magnitude due to elimination of coordinated water and the reduction of Tb-complex background luminescence.

Lanthanide ions are combined with a medium to be tested for endospores. A lanthanide chelate is produced by reaction with dipicolinic acid that is released from the endospores by either germination or destructive lysing; the lanthanide-dipicolinic acid complex has distinctive absorbance and emission spectra that can be detected using photoluminescence measurements. The concentration of spores can be determined by preparing a calibration curve that relates absorbance or emission intensities to spore concentrations for test samples with known spore concentrations.

In summary, the invention is defined as an improvement in sensitivity of a method of real time detection of endospores comprising the steps of combining lanthanide ions with a medium to be analyzed for bacterial endospore content. The lanthanide reacts with the dipicolinic acid released from bacterial endospores by either germination or destructive lysing (e.g., autoclaving, microwaving, oxidation) if present in the medium to form a lanthanide dipicolinic acid chelate. Any lanthanide chelate formed is excited with excitation energy distinctive of the lanthanide chelate. The existence of an emission which occurs at an emission wavelength distinctive of the lanthanide chelate as a result of the excitation is sensed. It is then determined whether bacterial endospores are present in the medium, based on the dipicolinic acid triggered emission.

More specifically, the improvement of the invention comprises the step of combining the lanthanide ion with the medium in the form of a lanthanide complex as the analysis reagent reacting with the endospores. The lanthanide complex is a any combination of the lanthanide ion with one or additional multidetente ligands, including without limitation supra- and supermolecules. The lanthanide complex comprises lanthanide cations encapsulated by ligands that enhance dipicolinic acid binding (i.e., cooperative binding). In one embodiment the lanthanide cations comprise terbium cations, and in another embodiment they comprise europium cations.

In the step of combining the lanthanide ions with the medium in the form of a lanthanide complex as the analysis reagent reacting with the endospores, the ligand that enables cooperative binding is usually multidentate (i.e., a ligand defined as having a coordination number of more than one and preferably 4-6) and allows only one dipicolinic acid molecule to bind to the endospore, thereby eliminating multiple equilibria and the resulting dipicolinic acid complex contains few to no coordinated water molecules. Preferably the terbium is provided in slight molar excess over its stoichiometric ratio to reduce background luminescence of uncoordinated terbium.

The invention is also alternatively defined as a method for determining the concentration of bacterial endospores present in a medium, the method comprising the steps of: combining a lanthanide complex as an analysis reagent with a sample medium; and determining the concentration of bacterial endospores present in the combined lanthanide complex and sample medium, based on the amount of lanthanide dipicolinate chelate resulting from the combination of lanthanide complex with the sample medium. The step of determining the concentration of bacterial endospores is performed using photoluminescence testing of the lanthanide dipicolinate chelate.

The step of determining the concentration of bacterial endospores comprises preparing a calibration curve that relates the luminescence intensity to the endospore concentration using photoluminescence testing of at least two, but preferably more, test sample media having different predetermined endospore concentrations; performing the photoluminescence testing on the sample medium with unknown endospore content to determine an absorbance intensity for the unknown sample medium; and relating the absorbance intensity for the unknown sample medium to an endospore concentration, and reading off the luminescence intensity from the calibration curve.

Defined alternatively, the step of determining whether the combined lanthanide complexes and sample medium includes a lanthanide dipicolinate chelate comprises exciting the sample medium and determining whether significant luminescence intensity increase occurs at wavelengths distinctive of the lanthanide chelate.

Defined in yet another way the step of determining whether the combined lanthanide complexes and sample medium includes a lanthanide dipicolinate chelate comprises exciting the sample medium and determining whether significant emission occurs at wavelengths distinctive of the lanthanide dipicolinate chelate.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 6 is a diagram depicting the synthesis of EZ for enhanced binding of DPA to $Tb^{3+}$ in solution.

FIG. 7 is a graph of the normalized luminescence intensity enhancement due to the binding of DPA to Tb3+ with EZ (right) and without EZ (left) as the total DPA concentration is varied from 10-4 to 10-8 M.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The molecular design considerations of the invention enhance the detection limit by over three orders of magnitude. The design features a complex comprised of a central lanthanide ion that is caged by a multidentate ligand that gives rise to cooperative binding of dipicolinic acid through additional binding interaction to the dipicolinic acid (e.g., hydrogen bonds or electrostatic interactions). Cooperative binding is defined as a net increase in binding constant of dipicolinic acid to lanthanide complexes binding with respect to dipicolinic acid binding to lanthanide ions (i.e., the lanthanide aquo complex). An increase in binding constant results in larger fractions of dipicolinic acid bound to the lanthanide molecules at low dipicolinic acid, which consequently increases the sensitivity of the bacterial spore assay since dipicolinic acid binding triggers lanthanide luminescence. In addition, the multi-dentate ligand serves to increase the quantum yield by an order of magnitude by eliminating coordinated water that effectively quenches the lanthanide luminescence. The multidentate ligand complex also eliminates multiple equilibria, which have forced previous investigators to use a large excess of lanthanide, which gives rise to large background luminescence due to free lanthanide ion. The lanthanides, Ln, include terbium, Tb, and europium, Eu. For the purposes of the illustrated embodiment Tb is chosen in specific examples, but any one of the lanthanides could be equivalently substituted.

Figure 3:
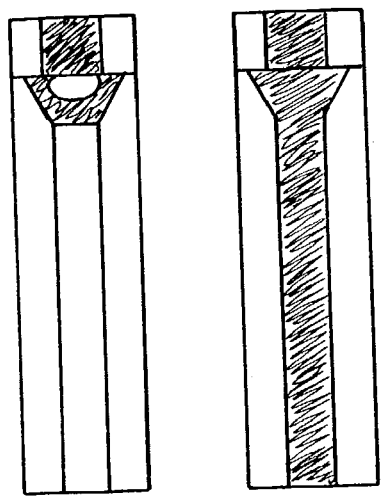
FIG. 3 is a photograph of two cuvets on a UV lamp.

The invention significantly improves the detection limit of bacterial endospore detection based on lanthanide dipicolinate luminescence. FIG. 3 is a photograph which shows a cuvet filled with 1-mM $TbCl_3$ (Tb cuvet), and another filled with 1-mM $TbCl_3$+1-μM DPA (Tb-DPA cuvet). Note the luminescence turn-on upon DPA addition. The amount of DPA in the Tb-DPA cuvet corresponds to 106 spores/ml. The specific advantage of this technique over traditional methods, such as stained spore microscopy and plate culture counting, is that it takes much less time to obtain quantitative spore analysis, namely a few minutes verses hours or days. Real time spore analysis is a valuable tool for NASA initiatives in planetary protection in the proof of spacecraft sterilization; environmental monitoring in closed loop life support systems, and astrobiology such as in testing the viability lifetime of spores.

Figure 1:
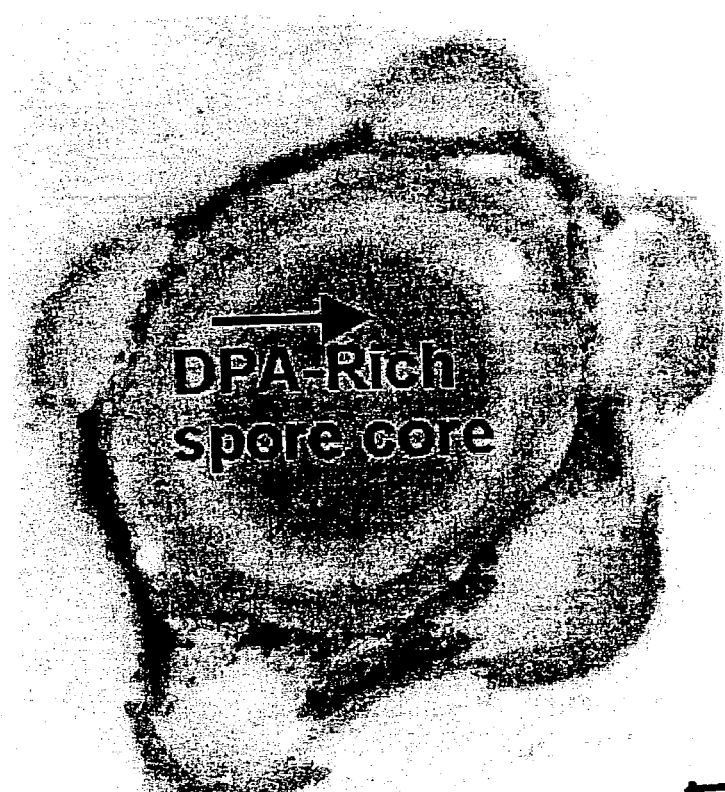
FIG. 1 is a microscopic image of a spore highlighting the DPA rich spore coat.

Recent investigations by Rosen et al. have produced a three-step lanthanide luminescence method for detecting and quantifying bacterial endospores, as disclosed in U.S. Pat. No. 5,876,960, which is incorporated by reference. $TbCl_3$ is added in excess to an aqueous suspension that contains bacterial endospores, which contain 2-15 wt % dipicolinic acid (DPA) as diagrammatically depicted in FIG. 1, which is a microscopic image of an endospore 10 in which the DPA rich coat 12 is highlighted. The $[Tb(H2O)9]3+$ reacts with DPA released from the spore casing to generate a monochelate $[Tb(DPA) (H2O)6]+$ complex. This complex exhibits enhanced luminescence intensity, relative to $[Tb(H2O)9]3+$, when excited with UV light at the DPA absorption maximum. Particulates are removed from the terbium-treated suspension by filtration using a 0.22 .mu.m filter. The luminescence intensity of the monochelate complex is then measured and correlated to a spore concentration by preparing a calibration curve of luminescence intensity against spore concentrations for test samples with known spore concentrations and reading off the luminescence intensity from the calibration curve.

The detection limit for Rosen's method is 1.2×105 CFU/ml where CFU is a colony forming unit. While lanthanide luminescence method of spore detection enables rapid quantitative analysis, the detection limit requires improvement, especially for applications in human health, e.g. monitoring air in surgical rooms, food quality etc. and planetary protection where there is a 300 spores/m2 standard for category IVa missions. As proposed below, these detection limits can be significantly improved by understanding (1) the binding properties of dipicolinic acid to lanthanide ion binding, (2) the photophysics of absorption energy transfer-emission (AETE) schemes illustrated in FIGS. 2a and 2b, and designing a lanthanide complex that optimizes the detection limit accordingly. Thus, it is to be understood that each and any of the basic processes disclosed in the Rosen method can be improved by the teachings of the invention as described below.

Figure 4:
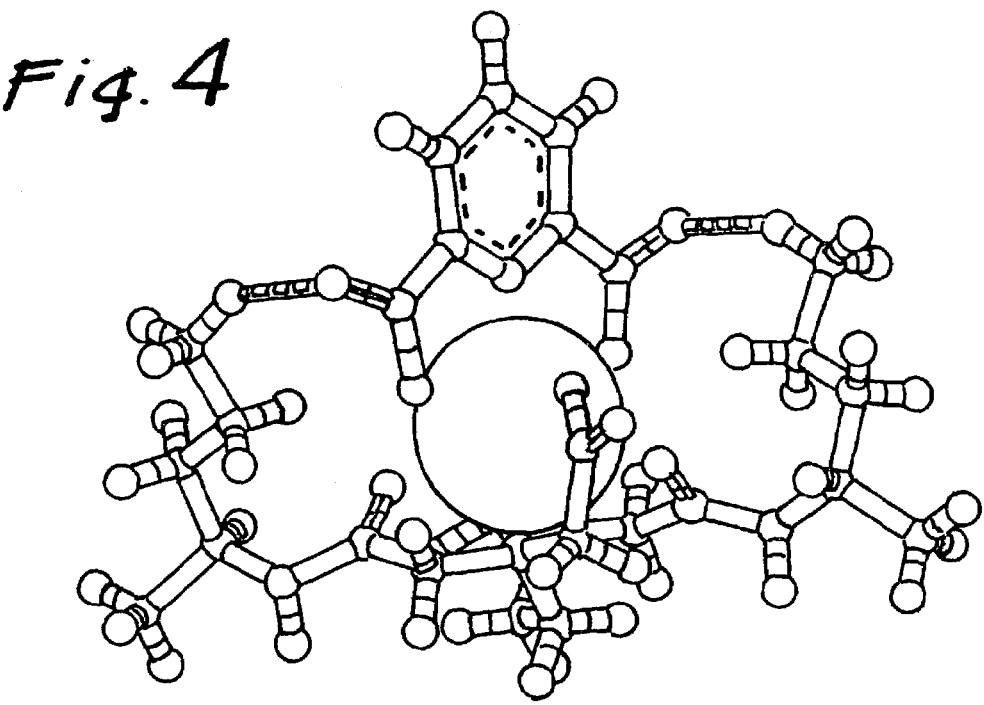
FIG. 4 is a three dimensional depiction of a model of a potential macrocyclic ligand bound to Tb.
Figure 5:
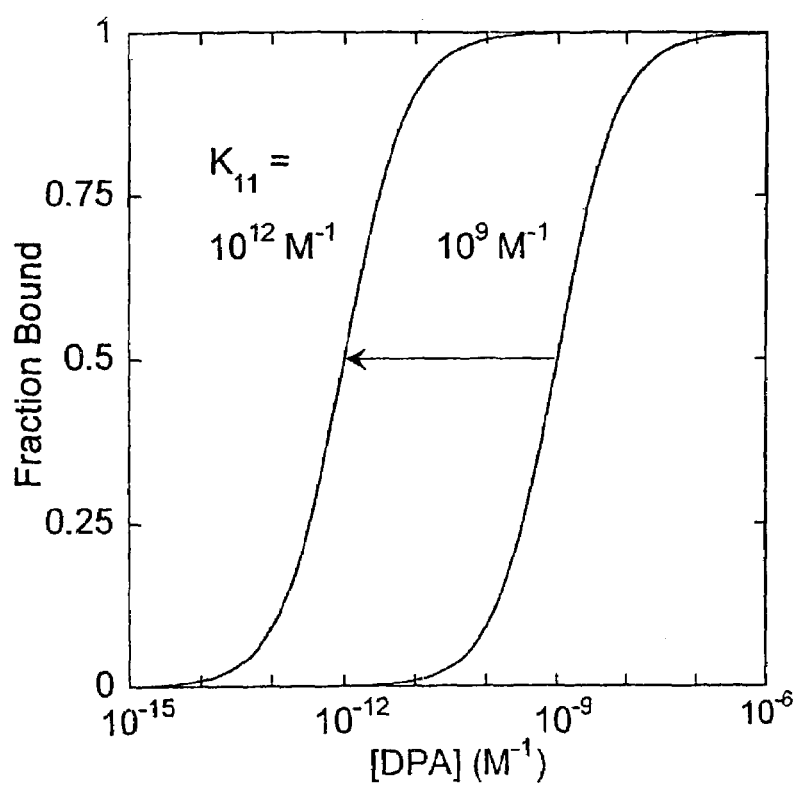
FIG. 5 is a graph where the fraction DPA bound to $Tb^{3+}$ is graphed against the concentration of DPA.

FIG. 4 is a three dimensional depiction of a model of a potential multidentate ligand bound to Tb with a guanidinium pendant group that can H-bond to an incoming DPA. The improvement of the detection limit enhanced by encapsulating the Tb with a multidentate ligand as shown in FIG. 4 that has hydrogen-bonding recognition sites for the incoming DPA is illustrated in the theoretical plot of FIG. 5 where the fraction DPA bound to $Tb3+$ is graphed against the concentration of DPA as the binding constant (K11) increases from 109 to 1012 M-1. A single bacterial spore that releases its DPA into 1 ml bulk solution results in a DPA concentration of 10-12 M. Thus, an increase in binding constant from 109 M-1 (when using $TbCl_3$) to 1012 M-1, by introducing interligand, intracomplex hydrogen bonding, will result in single spore per milliliter detection limits.

A problem governing the detection limit in the aforementioned method is the requirement for a great excess concentration of terbium over DPA. Excess terbium assures that predominantly monochelate $[Tb(DPA)aq]+$ is formed, out of the three possible Tb chelates $[Tb(DPA)n]3-2n$ for n=1,2,3 that exist in equilibrium. This is important, because each chelate has different photophysical properties, e.g. quantum yield, lifetime, and thus, a mixture of chelates complicates quantitative analysis. Unfortunately, the great excess of Tb required for forming monochelates also leads to a large, undesirable background luminescence due to unchelated $Tb3+$ luminescence, which adversely affects the detection limit. Moreover, the monochelate has 6 out of 9 coordination sites occupied with water. Coordinated water gives rise to efficient nonradiative decay pathways due to high frequency OH oscillators. These nonradiative decay pathways drastically reduce the luminescence quantum yield, which also adversely affects the detection limit.

Figure 2A:
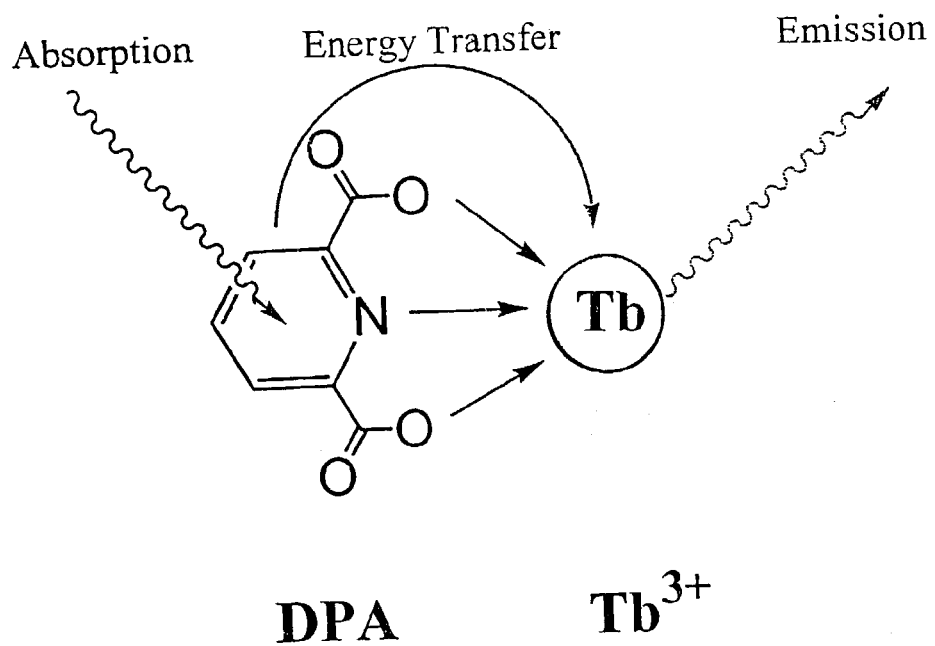
FIG. 2a is a molecular diagram of the crown ether encapsulation of 6 of 9 coordination sites of the luminescent $Tb^{3+}$ ion represented by the shaded ball. This complex has a low absorption cross section (<10 M-1 cm-1) and consequently luminesces poorly. The three remaining coordination sites of the Tb3+ crown ether complex can bind the light harvesting DPA, which has an absorption cross section >104 M-1 cm-1, originating from the spore. DPA binding gives rise to bright Tb luminescence.
Figure 2B:
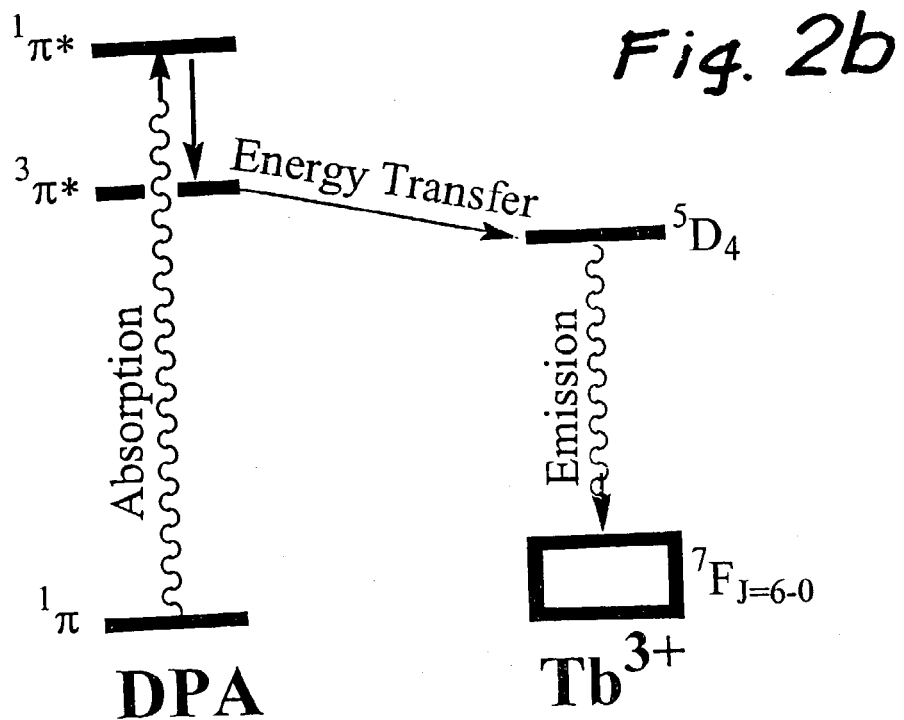
FIG. 2b is a diagram depicting the photo-physical scheme for DPA sensitized luminescence of the Tb-crown ether complex, i.e. the absorption-energy transfer-emission, AETE.

Ideally, the Tb would to be in slight excess to reduce the background luminescence of uncoordinated Tb, while simultaneously avoiding multiple equilibria and eliminating coordinated water. This can be accomplished by using a lanthanide complex as the analysis reagent according to the teaching of the invention as depicted in FIGS. 2a and 2b. The deleterious effects of coordinated water and multiple equilibria can be eliminated by encapsulating the lanthanide ions in multidentate ligands such as the one shown in FIG. 2a. The six coordinating atoms shown in the molecular structure occupy six out of nine coordination sites of the lanthanide ion. The presence of the remaining coordination sites of the $Ln3+$ crown ether complexes provides the opportunity for light-harvesting DPA to enter the coordination sphere, and be detected by the AETE process. Thus, a Tb-crown ether complex shown generally in FIG. 2a allows only one DPA molecule 18 to bind, i.e. multiple equilibria are eliminated, and the Tb-crown ether DPA complex of FIG. 2a contains no coordinated water.

In combination, the increased binding affinity of dipicolinic acid for lanthanide complexes capable of cooperative binding, elimination of coordinated water and multiple equilibria will result in an estimated 103-104 fold increase in sensitivity for the lanthanide luminescence method of bacterial spore detection.

FIG. 2b illustrates the AETE process. UV light is absorbed to excite the DPA molecule 18 in the combined form with the caged lanthanide from the state, $1\pi$ to $1\pi^*$. An energy decay to the $3\pi^*$ state of the DPA molecule 18 is followed by an energy transfer to the Tb-crown-ether complex in the 5D4 state. A characteristic energy decay or emission then follows from the 5D4 state in the Tb-crown-ether complex to the 7FJ=6-0 ground state.

The effect of chemical and biological interferents (not originating from endospores) has been studied extensively for this lanthanide Luminescence detection scheme and applies to the proposed scheme as well. It was found that no substance tested led to a false positive, which would occur if the intrinsic Tb luminescence is enhanced in the absence of bacterial endospores. However, false negatives occur when the signal of an endospore-containing sample is strongly inhibited. The main causes for luminescence inhibition are phosphate binding to Tb and interferents that absorb strongly at the wavelength of excitation. When such unknown interferents are present, the analytical capability is compromised. However, if calibration curves are performed with interferents present, then analytical ability remains intact, although the detection limit will be adversely affected.

The lanthanide dipicolinate luminescence method can be performed in minutes. With the 1000-10,000-fold improvement in detection limit obtained by implementing the novel supramolecular complex described in this report, new applications for spore detection can be realized. For example, spore detection is especially relevant to environmental monitoring of health care locations since many diseases are carried by *Bacillus, Clostridium,* including anthrax (*Bacillus anthracis*), tetanus (*Clostridium tetani*), botulism (*Clostridium botulinium*), and gas gangrene (several other *Clostridium* species).

Synthesis of one form of a lanthanide complex according to the invention is shown in the embodiment diagrammed in FIG. 6 where ethylene diaminetetraaceticacid zwitterion (EZ) molecule is depicted. In refluxing ethanol (2-aminoethyl)trimethylammonium chloride hydrochloride is insoluble, however the free base (2-aminoethyl)trimethylammonium chloride, is soluble, and is generated in solution with sodium hydroxide. A metathesis reaction occurs, and fine microcrystals of sodium chloride precipitate from the hot ethanol mixture, leaving an ethanol solution of the freebase (2-aminoethyl)trimethylammonium chloride. To this solution is added ethylene diamine tetra-acetic acid (EDTA) dianhydride, which reacts with the primary amine group of the two equivalents of (2-aminoethyl)trimethylammonium chloride. This reaction yields EZ in its carboxylic acid form. To produce the zwitterionic form of EZ, two extra equivalents of the free base amine are added to deprotonate this intermediate carboxylic acid yielding EZ and (2-aminoethyl)trimethylammonium chloride hydrochloride which is insoluble in ethanol and easily filtered away form the solution. It must be understood that many other forms and syntheses of lanthanide ions in the form of lanthanide complex are possible and expressly contemplated as being within the scope of the invention. Each of the alternative forms will combine with the medium as an analysis reagent which is capable of cooperative binding with dipicolinic acid from endospores to increase both the lanthanide-dipicolinic acid binding constant and the luminescence quantum yield.

The enhancement in the binding of a DPA molecule to the $Tb3+$ is the result of several factors at play in the ternary complex of a DPA molecule, a $Tb3+$ ion and EZ molecule. First the EZ molecule acts as a template or foundation capturing a $Tb3+$ with the amine and carboxylate groups at the core of the molecule to yield a complex $(EZ-Tb)3+$. Notice that the overall charge of this complex is 3+, but that two units of charge have effectively migrated out to the trimethylammonium groups at the ends of the molecule, which are not involved in the coordination the EZ molecule to the $Tb3+$ ion. FIG. 7 is a graph of the experimental data showing the enhanced intensity in detection of DPA (M) using the EZ molecule to complex with Tb.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for detecting bacterial endospores present in a medium comprising the steps of:

(i) constructing a standard curve by bringing together:
  a. a sample medium containing a known number of bacterial endospores; and
  b. a multidentate ligand lanthanide complex, wherein said complex is comprised of a multidentate ligand bound to a lanthanide ion, said multidentate ligand having recognition sites with attractive binding interactions for dipicolinic acid and facilitating the formation of a lanthanide dipicolinic acid complex wherein said lanthanide ion is a terbium or europium ion; and
  c. detecting a plurality of luminescence intensities at wavelengths distinctive of a lanthanide dipicolinic acid complex in the combined lanthanide complex and said medium comprising a known number of bacterial endospores, whereby a standard curve is obtained;

(ii) combining a sample medium containing an unknown number of bacterial endospores with the lanthanide-multidentate ligand complex in (i) b. above;

(iii) detecting a luminescence intensity resulting from said combining in step (ii) above; and (iv) obtaining the number of bacterial endospores in the sample medium from said standard curve obtained in step (i) above, comprising correlating the detected luminescence intensity with the endospore numbers on the standard curve.

2. The method of claim 1, wherein the calibration curve is obtained by relating luminescence intensities to known endospore numbers in at least two or a plurality of test samples.

3. A method to determine the number of bacterial endospores in a medium comprising the steps of:
   (i) constructing a standard curve by bringing together:
      a. a sample medium containing a known number of bacterial endospores; and
      b. a multidentate ligand lanthanide complex, wherein said complex is comprised of a multidentate ligand bound to a lanthanide ion, said multidentate ligand having recognition sites with attractive binding interactions for dipicolinic acid and facilitating the formation of a lanthanide dipicolinic acid complex wherein said lanthanide ion is a terbium or europium ion; and
      c. detecting a plurality of luminescence intensities at wavelengths distinctive of a lanthanide dipicolinic acid complex in the combined lanthanide complex and said medium comprising a known number of bacterial endospores, whereby a standard curve is obtained;
   (ii) combining a sample medium containing an unknown number of bacterial endospores with the lanthanide-multidentate ligand complex in (i) b. above;
   (iii) detecting a luminescence intensity resulting from said combining in step (ii) above; and
   (iv) obtaining the number of bacterial endospores in the sample medium from said standard curve obtained in step (i) above, comprising correlating the detected luminescence intensity with the endospore numbers on the standard curve,
   wherein at least one spore per ml in a medium containing bacterial endospores is detected wherein the detection limit is one spore per ml.

4. A composition of matter comprising a multidentate ligand bound to a lanthanide ion, the multidentate ligand having recognition sites with attractive binding interactions for dipicolinic acid wherein said lanthanide ion is a terbium or europium ion.

5. The method of claim 3, where binding dipicolinic acid with the multidentate ligand replaces lanthanide bound water.

6. The method of claim 3, where binding dipicolinic acid with the multidentate ligand reduces coordination sites for dipicolinic acid.

7. The method of claim 3, wherein the lanthanide complex comprises lanthanide cations.

8. The method of claim 3, wherein the lanthanide complex comprises terbium or europium cations.

* * * * *